(12) United States Patent
Gross

(10) Patent No.: US 9,439,996 B2
(45) Date of Patent: Sep. 13, 2016

(54) LIGHT SOURCE DISINFECTION IN A PNEUMATIC TRANSPORT SYSTEM

(71) Applicant: TRANSLOGIC CORPORATION, Denver, CO (US)

(72) Inventor: Daniel Robert Gross, Highlands Ranch, CO (US)

(73) Assignee: TRANSLOGIC CORPORATION, Denver, CO (US)

( * ) Notice: Subject to any disclaimer, the term of this patent is extended or adjusted under 35 U.S.C. 154(b) by 30 days.

(21) Appl. No.: 14/193,964

(22) Filed: Feb. 28, 2014

(65) Prior Publication Data
US 2015/0246152 A1    Sep. 3, 2015

(51) Int. Cl.
A61L 2/10   (2006.01)
A61L 9/20   (2006.01)
F24F 3/16   (2006.01)

(52) U.S. Cl.
CPC .. *A61L 9/20* (2013.01); *A61L 2/10* (2013.01); F24F 2003/1667 (2013.01); F24F 2003/1682 (2013.01)

(58) Field of Classification Search
CPC .................................. A61L 9/20; A61L 2/10
USPC ........................................ 422/120, 121, 24
See application file for complete search history.

(56) References Cited

U.S. PATENT DOCUMENTS

| | | | |
|---|---|---|---|
| 2,043,293 A | 6/1936 | Jennings | |
| 2,679,990 A | 6/1954 | Mathzeit et al. | |
| 2,710,728 A | 6/1955 | Halpern | |
| 2,773,658 A | 12/1956 | Van Otteren et al. | |
| 2,797,057 A | 6/1957 | Sindzinski et al. | |
| 2,815,182 A | 12/1957 | Mittag et al. | |
| 2,850,249 A | 9/1958 | Uderstadt | |
| 2,865,578 A | 12/1958 | Hennessy | |
| 2,893,660 A | 7/1959 | Cook et al. | |
| 2,943,814 A | 7/1960 | Mittag et al. | |
| 2,970,791 A | 2/1961 | Hafner et al. | |
| 2,997,253 A | 8/1961 | Mittag et al. | |
| 3,055,611 A | 9/1962 | Stout et al. | |
| 3,055,612 A | 9/1962 | Stout et al. | |
| 3,148,845 A | 9/1964 | Buchwald et al. | |
| 3,219,989 A | 11/1965 | Kuhrt et al. | |
| 3,223,353 A | 12/1965 | Kuhrt et al. | |

(Continued)

FOREIGN PATENT DOCUMENTS

EP    2082980 A1    1/2009

OTHER PUBLICATIONS

Aerocom GmbH & Co., Technical Bulletin: Empty Carrier Return Unit AC 3000 (CRU) Technical Information Manual, Mar. 4, 1996.

(Continued)

*Primary Examiner* — Sean E Conley
(74) *Attorney, Agent, or Firm* — Marsh Fischmann & Breyfogle LLP

(57) ABSTRACT

Provided herein are systems, apparatuses and methods for use in disinfecting pneumatic tube system (PTS) components and/or disinfecting air displaced during the operation of a PTS. More specifically, various aspects are directed to the use of light source disinfection systems for disabling bacteria, viruses and/or other micro-organisms (hereafter "pathogens") in a PTS. The light source disinfection systems allow of cleaning pneumatic carriers, cleaning the interior of pneumatic tubes and PTS components and/or cleaning air, which is used to propel pneumatic carriers in a PTS.

14 Claims, 12 Drawing Sheets

(56) References Cited

U.S. PATENT DOCUMENTS

| | | |
|---|---|---|
| 3,236,475 A | 2/1966 | Mach et al. |
| 3,238,515 A | 3/1966 | Schrader et al. |
| 3,265,325 A | 8/1966 | Buchwald et al. |
| 3,295,662 A | 1/1967 | Crosby et al. |
| 3,332,639 A | 7/1967 | Joy |
| 3,333,787 A | 8/1967 | Voitas et al. |
| 3,361,384 A | 1/1968 | Thorburn |
| 3,408,113 A | 10/1968 | Bouladon |
| 3,507,460 A | 4/1970 | Norman et al. |
| 3,627,231 A | 12/1971 | Kalthoff |
| 3,711,038 A | 1/1973 | Van Otteren |
| 3,813,058 A | 5/1974 | Smith et al. |
| 3,817,476 A | 6/1974 | Martin |
| 3,829,042 A | 8/1974 | Torochkov et al. |
| 3,892,372 A | 7/1975 | Hauber |
| 3,951,461 A | 4/1976 | De Feudis |
| 4,037,805 A | 7/1977 | Alexandrov et al. |
| 4,058,274 A | 11/1977 | Hochradel et al. |
| 4,084,770 A | 4/1978 | Warmann |
| 4,256,418 A | 3/1981 | Stangl |
| 4,354,775 A | 10/1982 | Jalas |
| 4,395,164 A | 7/1983 | Beltrop et al. |
| 4,437,797 A | 3/1984 | Kardinal |
| 4,509,123 A | 4/1985 | Vereen |
| 4,516,888 A | 5/1985 | Kardinal |
| 4,529,335 A | 7/1985 | Hilbert et al. |
| 4,563,112 A | 1/1986 | Mokuya et al. |
| 4,630,216 A | 12/1986 | Tyler et al. |
| 4,646,245 A | 2/1987 | Prodel et al. |
| 4,766,547 A | 8/1988 | Modery et al. |
| 4,786,229 A | 11/1988 | Henderson |
| 4,831,540 A | 5/1989 | Hesser |
| 4,941,181 A | 7/1990 | Igarashi et al. |
| 4,958,716 A | 9/1990 | Matsuo et al. |
| 4,971,481 A | 11/1990 | Foreman |
| 4,974,166 A | 11/1990 | Maney et al. |
| 5,038,290 A | 8/1991 | Minami |
| 5,097,421 A | 3/1992 | Maney et al. |
| 5,153,842 A | 10/1992 | Dlugos, Sr. et al. |
| 5,165,826 A | 11/1992 | Egbert |
| 5,166,884 A | 11/1992 | Maney et al. |
| 5,190,428 A | 3/1993 | Bryant et al. |
| 5,196,846 A | 3/1993 | Brockelsby et al. |
| 5,217,328 A | 6/1993 | Lang |
| 5,225,990 A | 7/1993 | Bunce et al. |
| 5,234,292 A | 8/1993 | Lang |
| 5,237,931 A | 8/1993 | Riedl |
| 5,260,694 A | 11/1993 | Remahl |
| 5,267,173 A | 11/1993 | Tanizawa et al. |
| 5,375,691 A | 12/1994 | Wirtz |
| 5,386,364 A | 1/1995 | Tyler |
| 5,434,790 A | 7/1995 | Saka et al. |
| 5,436,611 A | 7/1995 | Arlinghaus, Jr. |
| 5,562,367 A | 10/1996 | Scott |
| 5,655,677 A | 8/1997 | Fratello et al. |
| 5,661,743 A | 8/1997 | Nagai |
| 5,682,820 A | 11/1997 | Arata |
| 5,712,789 A | 1/1998 | Radican |
| 5,735,644 A | 4/1998 | Grosswiller et al. |
| 5,768,853 A * | 6/1998 | Bushnell .................. A23L 3/26 53/141 |
| 5,864,485 A | 1/1999 | Hawthorne et al. |
| 5,867,388 A | 2/1999 | Okumura et al. |
| 5,902,552 A * | 5/1999 | Brickley .................. A61L 2/10 250/455.11 |
| 5,959,568 A | 9/1999 | Woolley |
| 5,966,309 A | 10/1999 | O'Bryan et al. |
| 6,030,152 A | 2/2000 | Steele |
| 6,068,428 A | 5/2000 | Nair et al. |
| 6,076,652 A | 6/2000 | Head, III |
| 6,138,058 A | 10/2000 | Van Antwerp, Jr. et al. |
| 6,146,057 A | 11/2000 | Gromley et al. |
| 6,292,710 B1 | 9/2001 | Bonnet |
| 6,356,802 B1 | 3/2002 | Takehara et al. |
| 6,437,272 B2 | 8/2002 | Tamamoto et al. |
| 6,477,442 B1 | 11/2002 | Valerino, Sr. |
| 6,516,239 B1 | 2/2003 | Madden et al. |
| 6,539,360 B1 | 3/2003 | Kadaba |
| 6,659,693 B1 | 12/2003 | Perkins et al. |
| 6,665,586 B1 | 12/2003 | Ball et al. |
| 6,672,808 B1 | 1/2004 | McIntyre et al. |
| 6,702,150 B2 | 3/2004 | Sumetzberger |
| 6,711,463 B2 | 3/2004 | Tozuka et al. |
| 6,747,560 B2 | 6/2004 | Stevens, III |
| 6,762,382 B1 | 7/2004 | Danelski |
| 6,878,896 B2 | 4/2005 | Braginsky et al. |
| 6,887,358 B2 | 5/2005 | Elger |
| 6,911,910 B2 | 6/2005 | Sansone et al. |
| 6,939,088 B2 | 9/2005 | Farrell |
| 6,950,724 B2 | 9/2005 | Mileaf et al. |
| 6,959,229 B2 | 10/2005 | Eidemiller |
| 7,079,913 B2 | 7/2006 | Kato et al. |
| 7,092,788 B2 | 8/2006 | Brixius et al. |
| 7,104,734 B2 | 9/2006 | Smith et al. |
| 7,136,721 B2 | 11/2006 | Sano et al. |
| 7,151,980 B2 | 12/2006 | You et al. |
| 7,196,627 B2 | 3/2007 | Rommelmann et al. |
| 7,243,002 B1 | 7/2007 | Hoganson et al. |
| 7,328,084 B1 | 2/2008 | Hoganson et al. |
| 7,363,106 B2 | 4/2008 | Hoganson et al. |
| 7,953,515 B2 | 5/2011 | Hoganson et al. |
| 8,447,427 B2 | 5/2013 | Hoganson et al. |
| 8,565,915 B2 | 10/2013 | Dillon |
| 8,596,932 B2 | 12/2013 | Hoganson et al. |
| 8,641,329 B2 | 2/2014 | Barrios |
| 2001/0056311 A1 | 12/2001 | Valerino, Sr. |
| 2011/0097239 A1 | 4/2011 | Schmatz |

OTHER PUBLICATIONS

Telecom bedrifscommunicatie b.v. buispostsystemen (pneumatic tube systems)—tube-mail systems, Technical Manual, Radio Controlled Identifcation, Aug. 24, 1999.

* cited by examiner

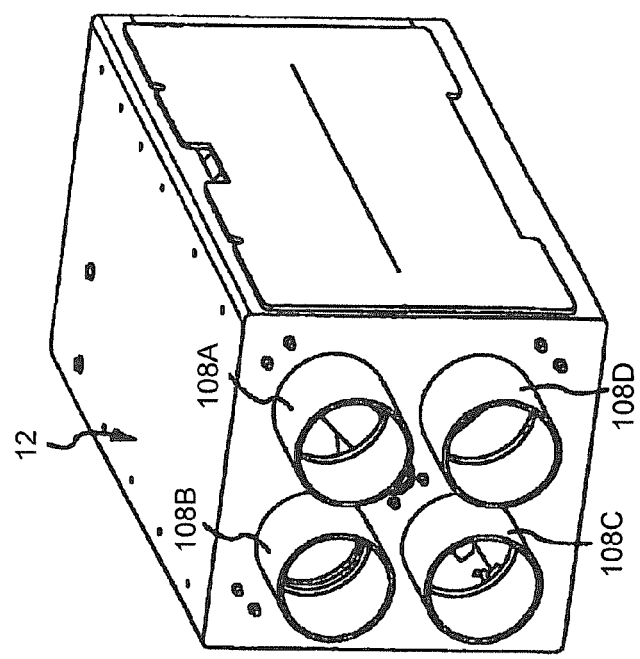

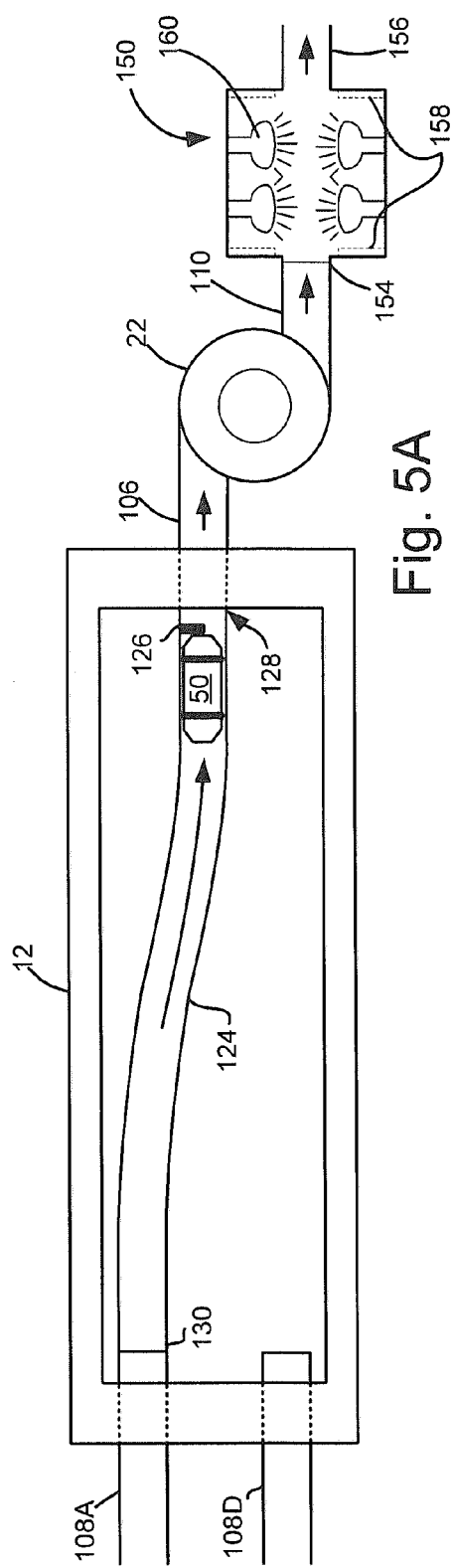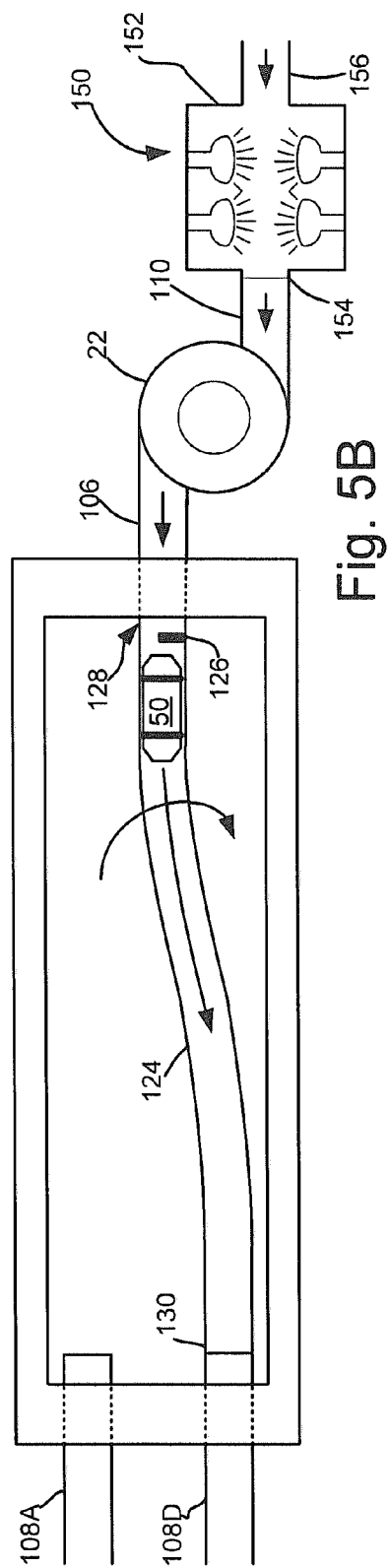

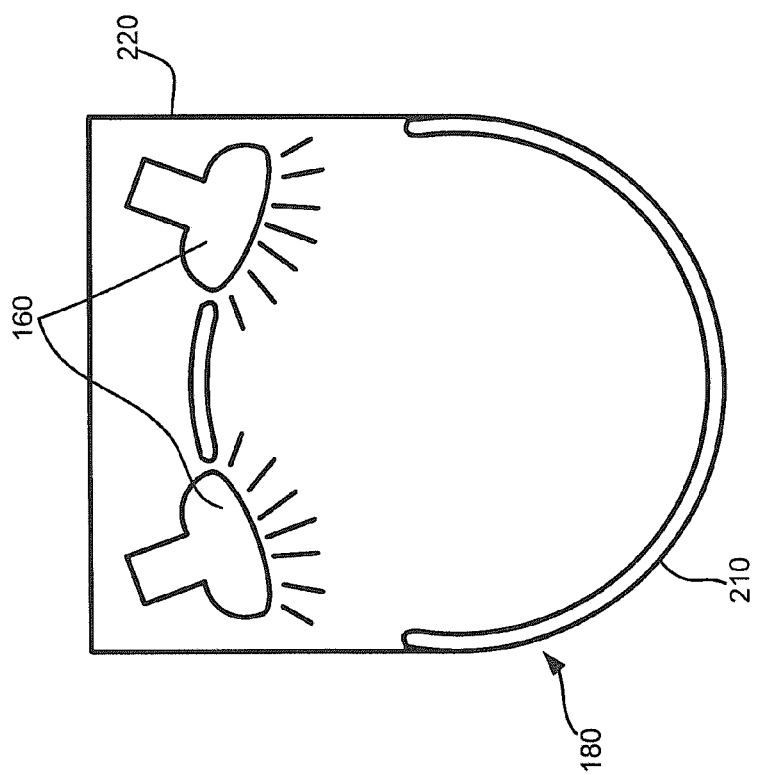

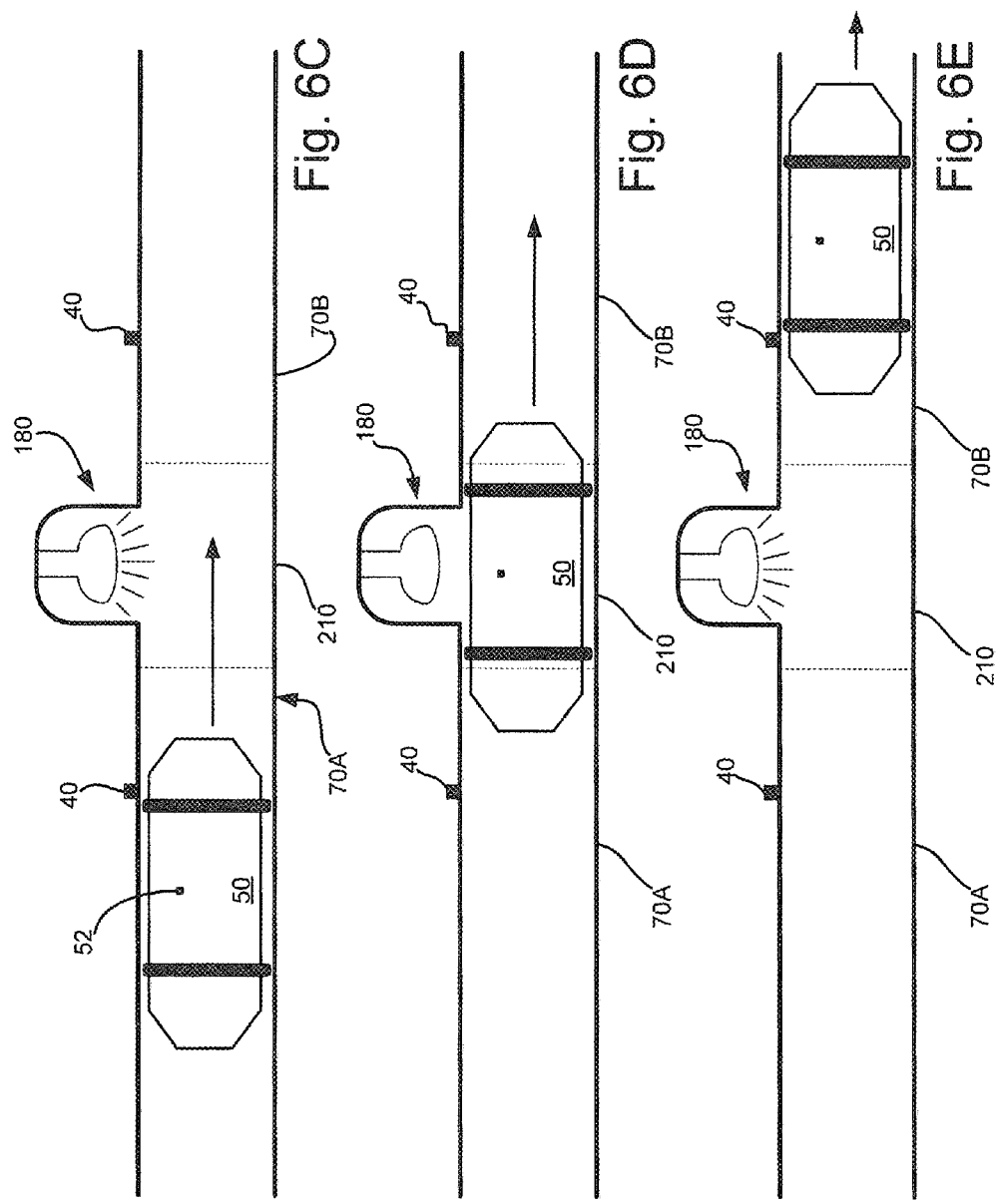

LIGHT SOURCE DISINFECTION IN A PNEUMATIC TRANSPORT SYSTEM

FIELD

The presented disclosure relates generally to pneumatic tube systems. More specifically, the disclosure provides systems, apparatuses, and methods for enhancing hygienic conditions of a pneumatic tube system and/or a facility incorporating a pneumatic tube system.

BACKGROUND

Pneumatic tube systems (PTS) are a well-known means for the automated transport of materials between, for example, an origination location and any one of a plurality of destination locations (e.g., stations). A typical PTS includes a number of pneumatic tubes interconnected in a network to transport carriers between user stations. Various air sources/blowers (or other pneumatic flow devices) and transfer units provide the force and path control means, respectively, for moving pneumatic carriers through and from tube-to-tube within the system. Generally, transfer units move or divert pneumatic carries from a first pneumatic tube to a second pneumatic tube in order to route the pneumatic carrier between locations, or stations, in the PTS.

The pneumatic carriers of a PTS may be utilized to transport various materials, which are disposed within the pneumatic carriers. In medical facilities, pneumatic carriers often transport patient-specific materials from one location to another (e.g. from pharmacy to nurse station; from operating room to laboratory, etc.). Materials transported by a medical facility PTS often include biological materials (e.g. urine, blood, spinal, tissue and other biological materials). It is desirable in such instances that such materials be isolated in a sterile fashion within various vessels (e.g. vials, syringes, bags, etc.) that are positioned within a pneumatic carrier during transport. However, leakage and other unintended spillage of such materials remains a concern. For example, the spillage of patient samples within a pneumatic carrier may introduce undesired microbes onto internal surfaces of the carrier. Further, in the event of leakage of materials outside of the pneumatic carrier, additional secondary contamination concerns arise. That is, if contents of a pneumatic carrier spill out of the carrier into a pneumatic tube of the PTS, subsequent carriers passing through the pneumatic tube are susceptible to cross-contamination. As such, in current pneumatic tube systems, carrier leakage typically results in a partial or total shut-down of the system to allow maintenance personnel to disinfect the tube system components. Typically, such disinfection requires the use of specialized carriers that spread liquid solvents/disinfectants throughout the portion of the PTS that is being cleaned.

SUMMARY

Aspects of the prevented inventions are based, as least in part, on the realization that pneumatic tube systems are often utilized in applications where sanitation is a primary concern. For instance, pneumatic tube systems are often utilized in hospital settings where numerous bacteria, virus and other pathogens exist. Accordingly, the potential of these pathogens contaminating pneumatic tube system components is of concern. Accordingly, provided herein are systems, methods, and apparatuses (i.e., utilities) directed to the reduction of pathogens in a pneumatic tube system. More specifically, the utilities disclose various embodiments and arrangements where light source disinfecting systems are utilized to reduce pathogens on or within pneumatic tube systems components and within the air displaced by a pneumatic tube system.

According to a first aspect, a utility is provided that allows for disinfecting pneumatic carriers utilized by a pneumatic tube system. The utility utilizes a pneumatic tube system component (e.g., light source disinfecting system/station) that is interconnected to the pneumatic tube system by one or more pneumatic tubes. Accordingly, pneumatic carriers from the pneumatic tube system may be transported to the station for disinfection. Typically, the disinfecting system includes a receiving tube for receiving pneumatic carriers from the pneumatic tube system. The receiving tube typically extends into an enclosed housing. Once the pneumatic carrier is received, one or more UV light sources (e.g., mercury lights, Xenon lights, etc.) apply UV light to surfaces of the pneumatic carrier. In one arrangement, pulsed UV light is utilized having a pulse duration of between about 0.01 milliseconds and about 3 milliseconds in duration. However, this is not a requirement and it will be appreciated that constant UV light may be applied as well.

In a further arrangement, the light source disinfecting system may be further operative to open a received pneumatic carrier such that UV light may be applied to the internal surfaces of the pneumatic carrier. As such as arrangement, the light source disinfecting system may receive the carrier open the carrier, apply UV light to the interior and/or out exterior surfaces of the carrier and then subsequently enclose the carrier and return the carrier to the pneumatic tube system.

In a further arrangement of the present aspect, the incorporation of the pneumatic carrier light source disinfecting system/station allows for periodic and/or scheduled maintenance of pneumatic carriers. For instance, a system control of the pneumatic tube system may utilize carrier identification information, which may be read from the pneumatic carriers, to periodically schedule disinfection. For instance, the system control may identify a number of carrier transactions performed by each carrier and, upon the number of carrier transactions exceeding a predetermined threshold, route the carrier to the light source disinfecting system. Alternatively, the system controller may route the carriers to the light source disinfecting system based on a predetermined schedule (e.g., every two days, etc.). Alternatively, the system controller may utilize input information received with a carrier transaction to determine if the carrier should be sent to the light source disinfecting system. For instance, upon carriers being sent to a lab in a hospital setting, the carrier may subsequently be routed the light source disinfecting system. That is, it may be assumed or known that the carrier has transported biological samples and that the carrier may benefit from disinfection. Alternatively, system users may manually send carriers to the light source disinfecting system by entering the light source disinfecting system as a carrier destination.

In another aspect, a utility is provided for cleaning interior surfaces of a pneumatic tube system. Specifically, the utility utilizes a modified pneumatic carrier (e.g., UV carrier) that is adapted to move through the pneumatic tube system. This UV carrier is operative to transport UV light sources throughout the pneumatic tube system such that UV light may be applied to interior surfaces of the pneumatic tube system. In one arrangement, the UV carrier includes a carrier body having first and second wear-bands that are attached to the carrier body at first and second spaced locations. These wear-bands may be sized for conformal receipt within the inside surface of a pneumatic tube. The first and second wear-bands in conjunction with the first and second ends of the carrier body block passage of air across the carrier body when disposed within a pneumatic tube. Accordingly, the UV carrier may move through a pneumatic tube system in a manner substantially identical to that of a standard pneumatic carrier. Supported along the body of the carrier and/or within the ends of the carrier, are one or more UV light sources, which direct light toward the inside surface of the pneumatic tube or other system component when the carrier body is disposed within the pneumatic tube system. A power supply is also supported by the carrier body, which that is operatively connected to the UV light sources to provide power for the same.

In a further arrangement, the carrier body may include one or more proximity sensors that allow for identifying when the carrier body is disposed within a confined surface. In this regard, such proximity sensors (e.g., photo detectors, etc.) may determine that the carrier is disposed within an enclosed surface such that it is safe to operate the UV light sources. As will be appreciated, it is typically desirable to prevent UV light sources from operating in the presence of system users due to safety concerns. Accordingly, the UV light sources may be controlled by a controller that only operates the UV light sources when the UV carrier is identified as being within the confines of a pneumatic tube or other system component.

In a further arrangement, the UV carrier may be utilized to disinfect pneumatic tube system components on a predetermined scheduled. That is, a system controller may be operative to periodically (or other schedule) route the carrier throughout the pneumatic tube system to disinfect interior surfaces thereof. In such an arrangement, carrier tracking devices (e.g., RFID tags, bar codes etc.) may be utilized to confirm and/or route the carrier throughout the system such that the system may be disinfected. In a further arrangement, it may be desirable to alter the speed of the pneumatic carrier as it passes through the pneumatic tube system. That is, it may be desirable to move the carrier at desired transit speed to apply UV light for a desired duration to the interior surface of the pneumatic tube system. Such duration may be based on one or more factors including, without limitation, the intensity of the UV light sources, the number of UV light sources, and/or the physical configuration of the UV carrier.

Another aspect of the invention is based on the realization by the inventor that the operation of a PTS not only transports a pneumatic carrier and its contents between system locations, but also transfers air between various locations in a facility. That is, during a carrier transaction, a pneumatic carrier is placed in a first station and a destination (e.g., second station) is identified for the carrier. A pneumatic tube connected to the station is then fluidly connected to the air source by aligning various transfer devices to connect pneumatic tubes between the air source and the station. At this time, the air source typically applies a vacuum to the pneumatic tube, which moves the carrier out of the station and into the pneumatic tube system. The carrier proceeds under vacuum until it reaches a turn-around location where the carrier is stopped. Various transfer devices are then realigned to connect pneumatic tubes, which provide a pneumatic path toward the ultimate destination of the pneumatic carrier. At this time, the air source typically provides positive air pressure to propel the pneumatic carrier from the turn-around location towards its ultimate destination through the realigned transfer devices and connected pneumatic tubes. Not only is the carrier transported between the first station and the second station, a portion of air drawn into the PTS from the first station location may be expelled at the second station location via the PTS. In the case of airborne contaminants or pathogens, a risk of airborne cross-contamination exists.

Another aspect of the presented utilities alleviate some of the risks associated with airborne cross-contamination through the use of light source disinfection. More specifically, some or all of the air displaced during a carrier transaction may be disinfected utilizing a light source disinfecting system. According one aspect, a utility is provided for disinfecting air that moves through a pneumatic tube system. In one arrangement, the utility is provided for disinfecting air that is drawn into or exhausted from the prime mover of the pneumatic tube system. As utilized herein, the prime mover is typically referred to as a blower. However, it will be appreciated any pneumatic pressure device may be utilized. What is important is that the prime mover/blower is operative to provide airflow to and/or from the pneumatic tube system to effect movement of carriers there through. In such an arrangement, the blower typically has a first port connected to the pneumatic tube system to provide airflow to/from the system and a second port for venting air from the blower and/or drawing air into the blower. A light source disinfecting system is interconnected to the second port through which air is vented and/or drawn into the blower. The light source disinfecting system included one or more UV light sources operative to apply UV light to the air vented from and/or drawn into the blower.

In one arrangement, the UV light source disinfecting system includes a housing having at least partially enclosed interior where the one or more UV light source are disposed within the interior of the housing. In various arrangements, the length and/or volume of the housing as well as the number of light sources may be selected to accommodate a desired flow rate for the blower. That is, the housing may be sized such that the flow rate through the housing results in air passing through the housing receiving UV light for a predetermined duration.

According to another aspect, an in-line light source disinfecting system is provided for use in a pneumatic tube system. In this aspect, a UV light disinfecting system may be incorporated into pneumatic tubes at one or more locations throughout a pneumatic tube system. Such an in-line UV light disinfection system allows apply UV light to airflow passing through a pneumatic tube. In this aspect, the utility includes a tube section having an internal bore that is aligned with internal bores of first and second pneumatic tubes such that a pneumatic carrier may pass through the light source disinfecting system. The tube section further includes one or more apertures further extending through its sidewall. UV light sources may be mounted proximate to these apertures such that UV light may be applied to the air passing through the internal bore of the tube section. In order to maintain pressure within the system, a housing or pressure jacket may surround the UV light sources and interconnect to the tube section.

In one arrangement, the in-line light source disinfecting system further includes one or more proximity sensors operative to identify an incoming pneumatic carrier. In such an arrangement, upon the carrier approaching the in-line UV light source disinfecting system, the UV light sources may be deactivated such that UV light is not be applied to a carrier as it passes through the light source disinfecting system. Such an arrangement may prevent application of UV light to contents of partially translucent and/or transparent pneumatic carriers.

BRIEF DESCRIPTION OF THE DRAWINGS

For a more complete understanding of the present disclosure and further advantages thereof, reference is now made to the following detailed description taken in conjunction with the drawings in which:

FIG. 4A illustrates a perspective view of a transfer unit that transfers a single tube to one of four interconnecting tubes.

FIGS. 5A and 5B illustrate FIGS. 4B and 4C which illustrates first and second sides view of the transfer unit with a connected blower and one embodiment of a light source disinfecting system.

FIGS. 6A-6F illustrates various views of an in-line light source disinfection system.

DETAILED DESCRIPTION

Reference will now be made to the accompanying drawings, which at least assist in illustrating the various pertinent features of the presented inventions. In this regard, the following description is presented for purposes of illustration and description. Furthermore, the description is not intended to limit the disclosed embodiments of the inventions to the forms disclosed herein. Consequently, variations and modifications commensurate with the following teachings, and skill and knowledge of the relevant art, are within the scope of the presented inventions.

Provided herein are systems, apparatuses and methods for use in disinfecting pneumatic tube system (PTS) components and/or disinfecting air displaced during the operation of a PTS. More specifically, various aspects of the presented inventions are directed to the use of light source disinfection systems for disabling bacteria, viruses and/or other microorganisms (hereafter "pathogens") in a PTS. The light source disinfection systems allow of cleaning pneumatic carriers, cleaning the interior of pneumatic tubes and PTS components and/or cleaning air, which is used to propel pneumatic carriers in a PTS.

Pneumatic Tube System

Figure 1:
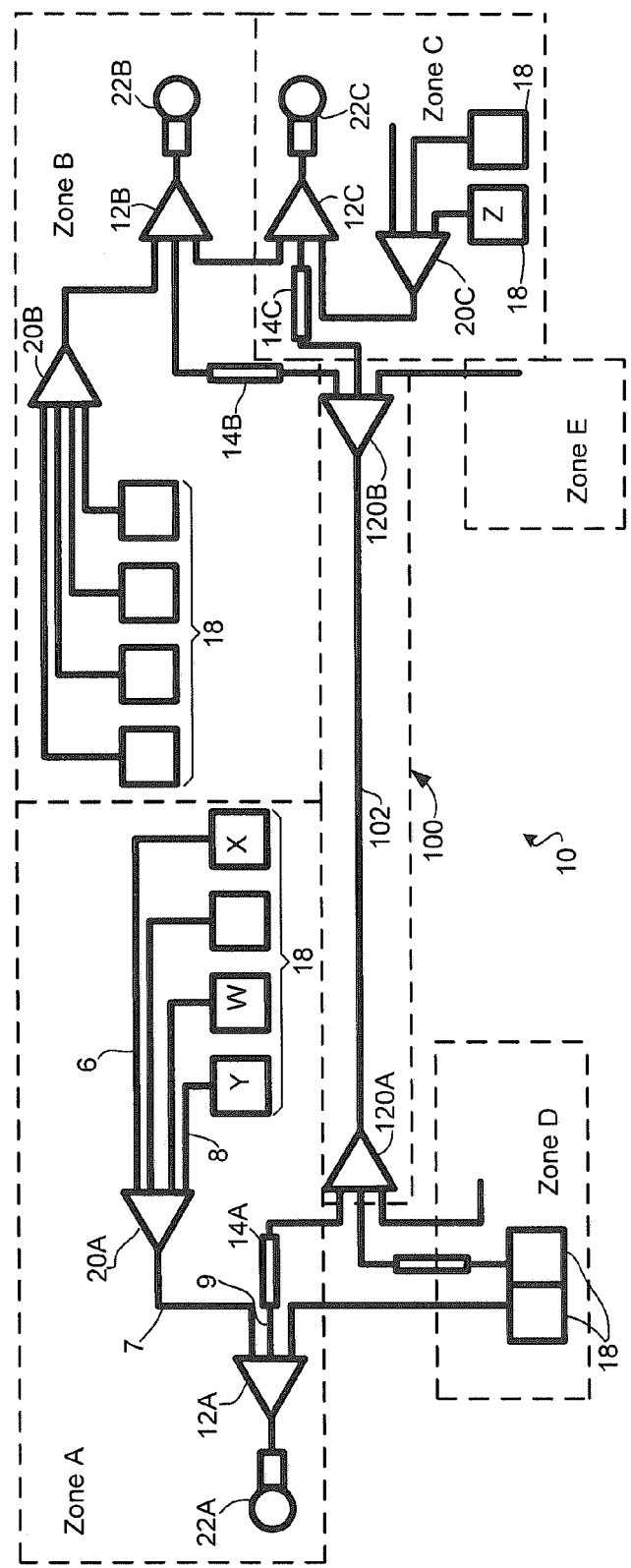
FIG. 1 illustrates one embodiment of a pneumatic tube system.

FIG. 1 illustrates an exemplary system diagram for a pneumatic tube system (PTS) 10. The PTS 10 is divided in to various zones each of which includes various system components. For example, Zone A includes components 12A, 20A etc. Unless discussing a component of a specific zone (e.g., component 12A), the common components of each zone are generally referred to without the zone suffix (e.g., component 12 refers to component 12A, 12B etc.). In general, the PTS 10 transports pneumatic carriers between various user stations 18, each such transport operation being referred to herein as a "transaction". At each of the user stations 18, a user may insert a carrier, select/enter a destination address/identification and/or a transaction priority, and then send the carrier. The PTS 10 determines a path to route the carrier and begins directing the carrier through the system.

Figure 2:
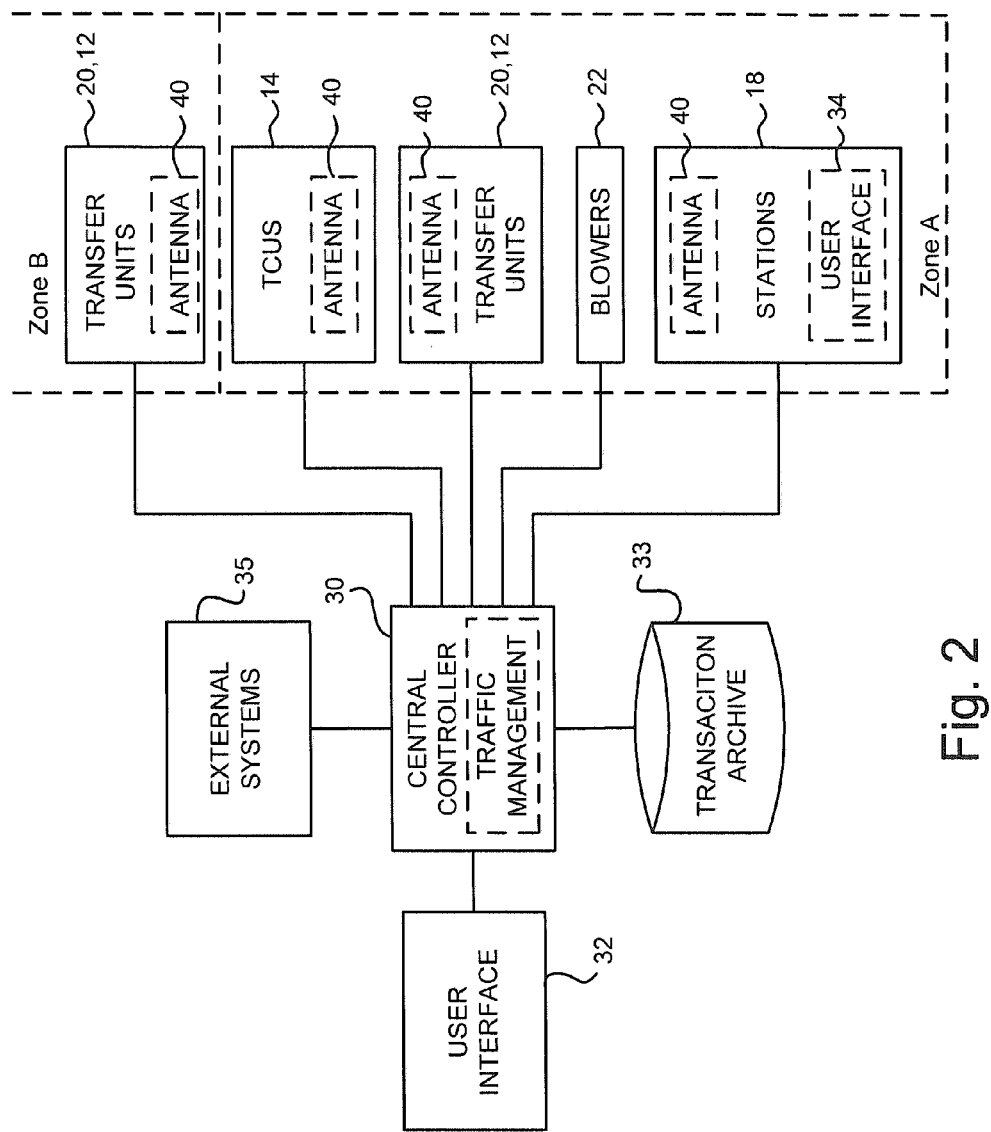
FIG. 2 illustrates a control system for use in controlling a pneumatic tube system.

Interconnected with most stations 18 is a pass-through transfer unit 20 which orders carriers arriving through different tubes from different stations 18 into a single pneumatic tube or diverts carriers a carrier arriving through the single tube into one of the different tubes connected to the stations. The pass-through transfer unit is connected by the single tube to a vacuum turn-around transfer unit 12 and an air displacement mechanism or blower 22 that provides the driving pneumatic force for carrier movement. The turn-around transfer unit 12 receives a carrier trough one of multiple pneumatic tubes, holds the carrier therein and redirects the carrier back out one of the multiple tubes once realigned. A set of transfer units 12, 20, a blower 22 and one or more stations 18 typically define a single zone (e.g., zones A, B, C, etc.). In the present embodiment, the turn-around transfer unit 12 is a point of connection to each zone and the zone connection point for each blower 22. However this is not a requirement. Within the system 10 itself, one or more devices are employable for ordering and routing carriers to their selected destinations. One type of device is a traffic control unit (TCU) 14 which is employable to receive, temporarily store and controllably release one or more carriers. Such functionality allows, for example, holding a carrier until a path through a subsequent portion of the system becomes available All of the components described in FIG. 1 electronically connect to a central controller which controls their operation. Disclosed in FIG. 2 is an electrical system diagram for the pneumatic carrier system 10 described herein. Providing centralized control for the entire pneumatic carrier system 10 is a system central controller (SCC) 30. The SCC 30 may include a digital processor and memory. SCC 30 may be configured as one or more programmable digital computers. Connectable to the SCC 30 may be one or more user interfaces 32, 34 through which a system user may monitor the operations of the system and/or manually enter one or more commands to control its operation. Typically, at least one user interface 34 is located at or within an area serviced by stations 18. For example, in a medical facility application, one or more user stations 18 and at least one user interface 34 may be provided within each emergency room, laboratory, nursing station, etc. In this regard, the user interface may be contained in the stations 18, or be stand-alone units.

Each of the components described above in relation to FIG. 1 may include one or more electrical and/or electro-mechanical components which provide for the physical movement of a carrier within the system 10 and/or the obtainment/provision of information relating to the location of the carriers within the system 10. In this regard, the components shown in FIG. 2 are representations of the various electrical and electro-mechanical systems that may be employed by the pneumatic carrier system 10. Although in FIG. 2 they are represented single blocks, one skilled in the art will realize that the block for each type of device represents the electronics for a number of the same or similar type of components positioned throughout the system which provides for its operation. In various embodiments, each of the user stations 18, TCUs 14, transfer devices 20, 12 and/or pneumatic tubes may incorporate antenna devices/readers 40 configured to read or energize and retrieve identification information from identification devices such as bar codes, ID chips (e.g., RFID), etc. that may be incorporated into each of the carriers. Such an identification/tracking system is set forth in co-assigned U.S. Pat. No. 7,243,002, the contents of which are incorporated herein by reference.

Referring again to the electrical system diagram of FIG. 2, it may be seen that various transfer units 12, 20, and blowers 22 are also electrically connectable to the SCC 30. Through these connections, SCC 30 may send command signals to these devices so that they are actuated and operating at particular times and in particular sequences to affect the completion of the various carrier transactions. Other signals exchanged may include various monitoring signals that indicate the devices are operating as desired.

The SCC 30 is further connectable to a transaction archive 33, or database, which is configured to store transaction information for carriers moving within the system 10. The transaction information may include identification information for carriers moving through the system and destination information entered by a system user. Further, the transaction information may include sender identification, recipient identification, security information (e.g., PIN numbers) and/or location information obtained via tracking inputs received from antenna devices/readers 40 located at user stations 16, 18, TCUs 14, pneumatic tubes or other components along the travel path of a given carrier. The external systems 35 connected may depend on the purpose of the pneumatic carrier system 10. For example, the external systems 35 may include a lab information system, a pharmacy information system, a patient information system, a security information system and/or messaging systems (e.g., email, text, paging, or wireless system, etc.).

Pneumatic Carrier

Figure 3:
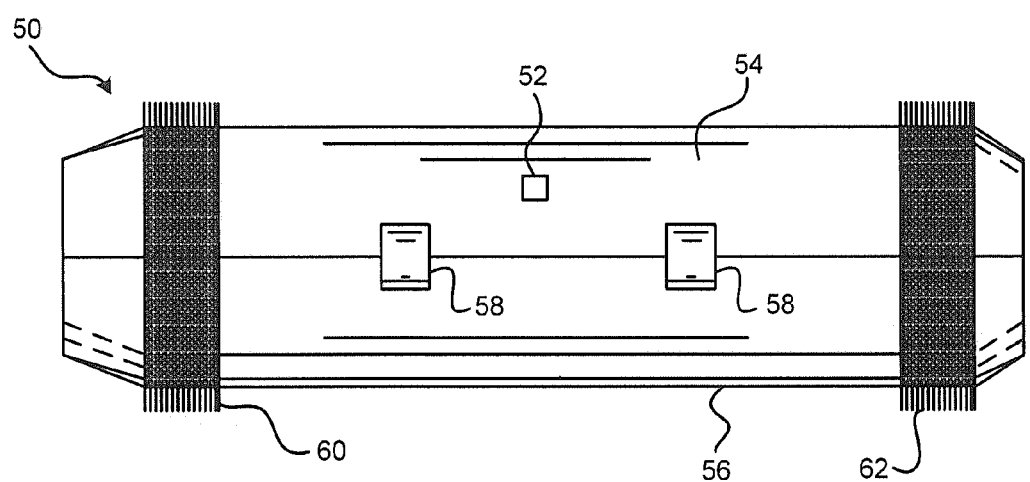
FIG. 3 illustrates one embodiment of carrier for use in a pneumatic tube system.

One type of carrier 50 that may be utilized with the PTS 10 is illustrated in FIG. 3 and includes first and second shell members 54 and 56 that collectively define an enclosed space for use in carrying materials as they are transported through the system 10. These shell members 54, 56 are adjoinably cylindrical in cross-section for use in correspondingly cylindrical pneumatic tubes of the system 10. The shell members 54 and 56 may be pivotably interconnected by a hinge member (not shown), and latches 58 may be provided for securing the first shell member to the second shell member in a closed configuration. Also included as part of the carrier 50 are wear bands 60, 62. The wear bands 60, 62 are sized to snuggly fit within the inside surface of the pneumatic tubes in order to substantially block the passage of air across a carrier 50 within such a pneumatic tube. Accordingly, this blockage results in a pressure differential across the carrier 50 in the presence of an airflow, which results in the carrier 50 being pushed or drawn through the pneumatic tube. In the illustrated embodiment, an ID chip 52 (e.g., RFID, bar code, etc) is attached to one of the shell members 54. In this regard, antenna device/readers may be incorporated into system components and/or pneumatic tubes within the system 10 to monitor the location and/or translocation of the carrier through the system. In a further embodiment, an ID chip or element may be attached to an item (e.g., payload) disposed within the interior of the carrier 50. In such an arrangement, the carrier itself may or may not include such an ID chip. What is important is that the carrier or its contents may be identified as they pass through the system. Accordingly, transaction information (e.g., destination information) associated with the identification read from the carrier or its contents may be cross-referenced at multiple locations throughout the system. Such cross-referencing may prevent the misdirection or erroneous delivery of a carrier transaction. Further, use of the carrier ID may allow for scheduling carrier maintenance, as is more fully discussed herein.

PTS Operation

Referring again to FIG. 1, an exemplary inter-zone transfer is discussed in relation to movement of a carrier from station 18X in Zone A to station 18Z in Zone C. Initially, a user inserts a carrier into station 18X and requests transfer to station 18Z. The system controller operates the blower 22A of Zone A to provide vacuum to station 18X. This requires aligning the internal tubing of the turn-around transfer unit 12A and the transfer unit 20A to the pneumatic tube 6 connecting station 18X to the transfer unit 20A. Once aligned, the blower applies vacuum to the aligned tubing and the carrier is drawn into the pneumatic tube 6. The carrier passes through the pass-through transfer unit 20A into pneumatic tube 7 and is received in the turn-around transfer unit 12A, which stops and holds the carrier during realignment. At this time, internal tubing of turn-around transfer unit 12A may be aligned with the output tube 9. Once aligned, blower 22 provides positive air pressure behind the carrier, which displaces the carrier from the turn-around transfer unit 12A and into tube 9. The carrier is received by TCU 14A where it awaits delivery into the inter-zone transfer unit 100 which interconnects different zone of the pneumatic tube system. Alternatively, the carrier may pass directly through the TCU 14A if all downstream components are aligned. As shown, an inter-zone transfer unit 100 connects Zone A and Zone C. The inter-zone transfer unit 100 utilizes opposing pass-through transfer units 120A, 120B having head ends (e.g., single port inlets) connected by a single connecting tube 102, which may be of considerable length. The output ends of the opposing pass-through transfer units 120A, 120B are each selectively connectable to multiple tubes that may be connected to different zones and/or stations. Other embodiments may use dedicated one-way transfer tubes between different zones as disclosed by co-owned U.S. Pat. No. 7,243,002 as incorporated above. In the present example, the opposing pass-through transfer units 120A, 120B are aligned to interconnect Zone A with Zone C.

The carrier exits the TCU 14A and is directed through the interzone transfer unit 100 under positive pressure provided by the blower 22A of zone A and proceeds until it is received by a TCU 14C in Zone C. At this time, the blower 22A of Zone A has completed its part of the transaction and may be utilized to perform other pending transactions for Zone A. The blower 22C of Zone C provides vacuum to the carrier disposed in the TCU 14C to move the carrier into the turn-around transfer unit 12C. The turn-around transfer unit 12C is then realigned to provide the carrier to transfer unit 20C, which is aligned with desired station 18Z. Accordingly, the blower 22C may provide positive pressure to move the carrier out of the turn-around transfer 12C, through the transfer unit 20C and to station 18Z.

Air Transfer Between Stations

One aspect of the present disclosure is based upon the realization that the operation of the PTS not only transports the pneumatic carrier 50 and its contents between system locations (e.g., stations), but may also transfer air between various locations in a facility. That is, upon applying air pressure (e.g., vacuum) to a carrier at a first/origination station to move the carrier into the PTS, air from the location of the first station is drawn into the PTS 10 until, for example, the carrier reaches a turn-around location where the carrier is stopped. Once the PTS is realigned to provide a pneumatic path toward the ultimate destination of the pneumatic carrier, air flow (e.g., positive air pressure) is provided to propel the pneumatic carrier from the turn-around location towards its ultimate destination. Not only is the carrier transported between the first station and the second station, a portion of air drawn into the PTS from the first station location may be expelled at the second station location via the PTS. In the case of airborne pathogens, a risk of cross-contamination exists.

Figure 4B:
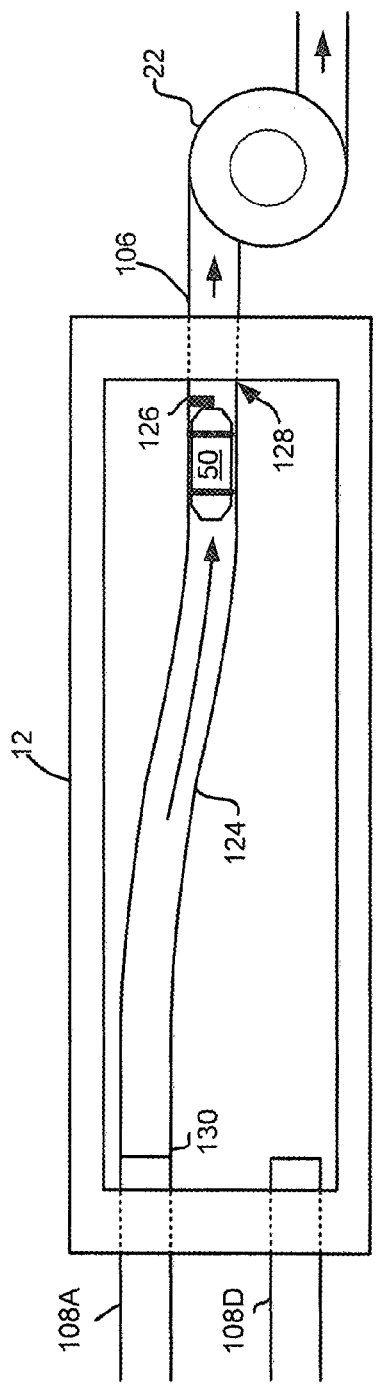
FIGS. 4B and 4C illustrate first and second sides view of the transfer unit with a connected blower.
Figure 4C:
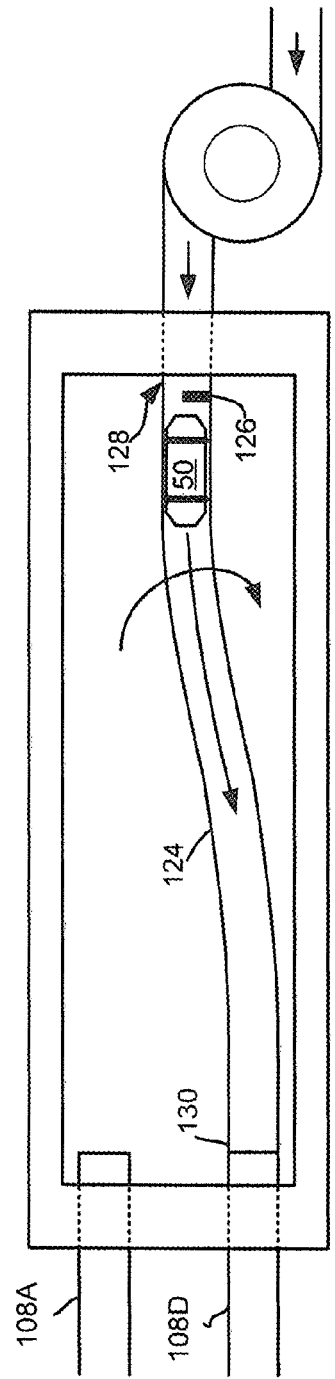

FIGS. 4A, 4B and 4C illustrate a perspective and side view of a turn-around transfer unit 12 and blower 22 and the exhausting and injection of air during vacuum and pressure cycles of the blower 22. As shown, the transfer unit 12 is a diverting unit that allows for transferring a received carrier between any one of four inlet/outlet four ports 108A-108D that enter into one end of the transfer unit 12. An air source port 106 is disposed on an opposite end of the transfer unit 12, which is connectable to an air source/blower 22 that provides bi-directional air flow. Though discussed in relation to a four port device, it will be appreciated that other devices may utilize more or fewer inlet/outlet ports. To effect transfer of a received carrier between two of the inlet/outlet ports, the transfer unit 12 includes a transfer tube 124. As shown in FIG. 4B, the transfer tube 124 is a bent or offset tube that may be selectively positioned between the head end or air source port 106 connected to the air source and any one of the four inlet/outlet ports, each of which is connected to separate tubes that may be connected to different zones, stations etc. In this regard, the transfer tube 124 is typically a curved tube having a head end 128 rotatively coupled to the air source port 106 and a transfer end 130 that is operative to rotate into an adjacent position with any one of the inlet/outlet ports. Generally, a motor (not shown) is interconnected proximate to the head end of the transfer tube 124 that is operative to rotate the tube utilizing, for instance, sprockets, gears, etc.

In operation, the transfer end 130 of the transfer tube 124 is positioned adjacent to one of the inlet/outlet ports 108A and air flow is initiated into the transfer unit 12 (e.g., a blower may provide airflow in a first direction) such that a carrier 50 may drawn into the transfer unit 12 via the connected port 108A. The carrier 50 moves into the transfer tube 124 until it reaches a stop 126 that extends into the bore of the transfer tube 124 and impedes movement of the carrier 50. During this process, the blower 22 draws air into the transfer unit 12 through the aligned pneumatic tubes connecting the transfer unit 12 to the origination location of the carrier 50. This air is exhausted/vented through an inlet/outlet air port 110 of the blower 22. Typically, the air is vented into a room that may house multiple blowers.

The offset transfer end 130 of the transfer tube 124 may then be rotated to an adjacent position with any one of the four inlet/outlet ports (e.g., port 108D). See FIG. 4C. At this time, air flow may be reversed (e.g., a blower may provide air flow in a second direction) to expel the carrier through the transfer tube and out of the connected port 108D. More specifically, the blower 22 draws air into the inlet/outlet port 110 to provide the pressurized air flow. Accordingly, air that was vented by the blower (i.e., from the carrier origination location) may be drawn back into the blower to provide the pressurized air flow that propels the carrier to a downstream location and/or is final destination. Further, if multiple blowers of multiple zones are disposed in a common area, air expelled from any of the blowers may be drawn into the blower providing the airflow that propels the carrier.

Light Source Disinfection

To alleviate concerns relating to cross-contamination resulting from the transfer of air between PTS locations, one embodiment of the presented systems a light source disinfecting system 150 that treats air that is vented from and drawn into a PTS blower 22. More specifically, the presented system utilizes Ultraviolet (UV) light for disinfecting the air. Ultraviolet germicidal irradiation (UVGI) is a disinfection method that uses ultraviolet (UV) light at sufficiently short wavelength to kill microorganisms/pathogens. It is effective in destroying the nucleic acids in these organisms so that their DNA is disrupted by the UV radiation, leaving them unable to perform vital cellular functions. Typically, the high-energy ultraviolet light in the area of the spectrum known as UV-C (e.g., UV wavelengths between about 240 nm and 290 nm) is utilized for disinfection. Such UV-C light is typically produced by either mercury or xenon gas lamps. The UV-C energy generated by such lamps passes through the cell walls of bacteria, viruses, bacterial spores and other pathogens.

Optimal wavelengths vary for UV-C disinfection of different organisms. On average, wavelengths of 260-265 nm are where peak DNA absorption occurs. However, wavelengths between about 260 nm-280 nm are considered to be the germicidal/disinfecting range of UV-C. The most common form of UV is produced by mercury vapor lamps. In these lamps, the mercury vapor is excited to create continuous UV-C at a wavelength around 254 nm. UV-C can also be produced by pulsing a xenon lamp. This method produces a flash of light containing a broad UV spectrum (from 200 nm to 320 nm) covering the entire germicidal UV band, delivered in millisecond pulses. The broad spectrum nature results in more UV-C wavelengths being produced. Combined with the high intensity of the millisecond pulses, pulsed xenon UV is believed to provide disinfection efficacy several times faster than mercury UV. Accordingly, preferred embodiments of the light source disinfecting system 150 utilize pulsed xenon UV sources. However, any appropriate UV source may be utilized.

As shown in FIGS. 5A and 5B, the light source disinfecting system 150 is interconnected to the inlet/outlet air port 110 of the blower 22. In the illustrated embodiment, the light source disinfecting system 150 includes an enclosed housing 152 that supports one or more UV light sources 160. A first port 154 of the housing 152 is directly interconnected to the inlet/outlet air port 110 of the blower 22. A second port 156 of the housing 152 is provided to vent/exhaust air from the blower 22 or draw air (e.g., atmospheric air) into the blower 22. In either situation, air exhausted from or drawn into the blower 22 passes through the interior of the enclosed housing 152 where it is exposed to the UV light sources 160. Typically, multiple UV light sources 160 are provided such that all air passing through the housing 152 is exposed (e.g., direct line of sight) to one or more of the UV light sources. Furthermore, various shielding may be provided to prevent exposure of any UV light outside of the housing 152. For instance, the second port 156 of the housing may include one or more bends (not shown) to prevent direct line of sight outside of the housing.

The number of UV light sources 160 as well as the length of the housing 152 may be sized to accommodate specified airflow through the housing 152. That is, the housing 152 in light sources 160 may be adapted to provide adequate UV light for disinfecting a predetermined airflow into or from the blower 22. Stated otherwise, disinfection is a function of UV concentration and time and the light source disinfection system 150 may be sized to accommodate a desired airflow while providing a desired level of disinfection. Further, the housing may include various filters to remove airborne particles. Additionally, the UV light source system may incorporate an ion generator having charged plates/electrodes 158 that generate a charge in ions of particles in the air passing through the housing. In such an arrangement, the charged ions may be attracted to one of the electrodes. Such a system may reduce build up of contaminates on the UV light sources. However, the UV light sources and/or electrodes may each require periodic cleaning.

Figure 6A:
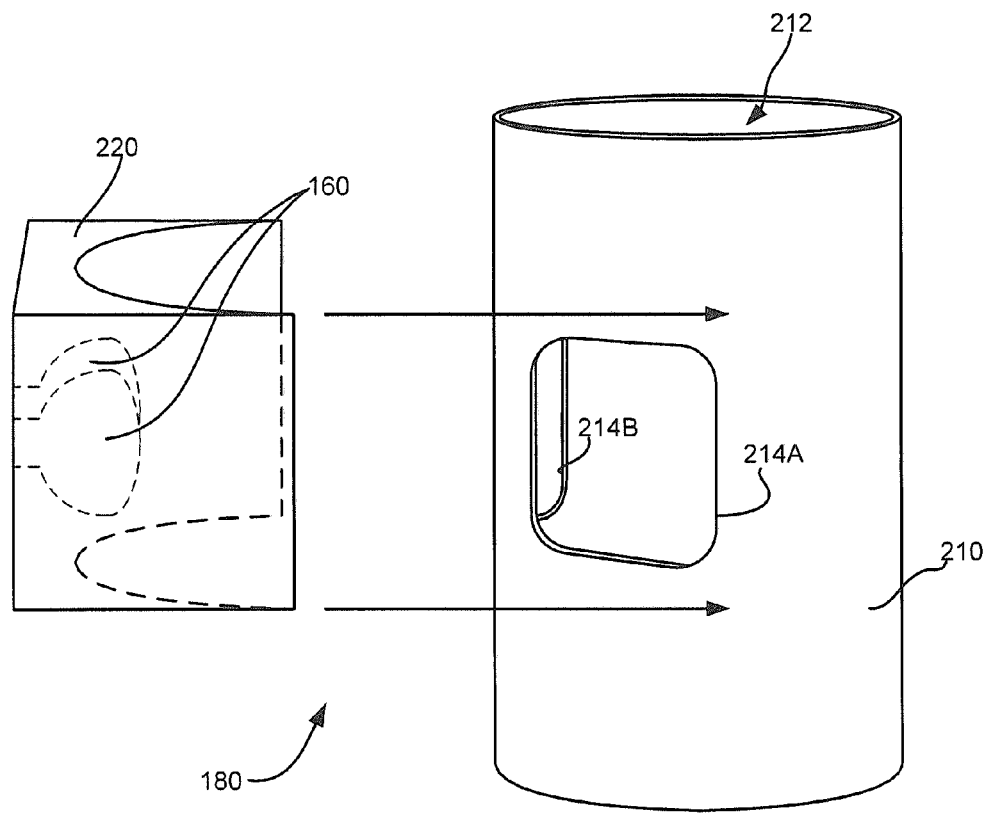
Figure 6F:
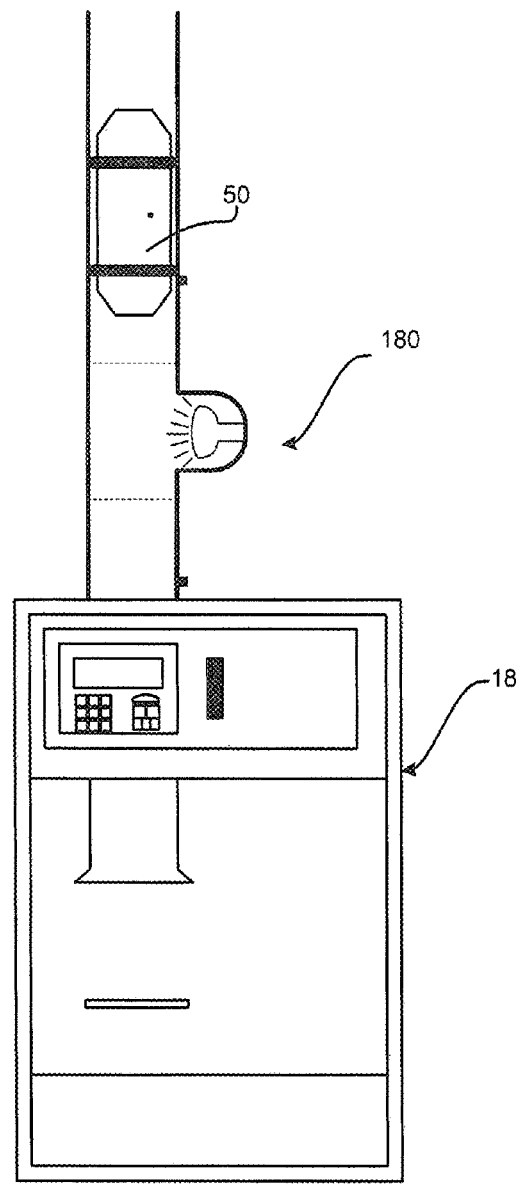

FIGS. 6A-6F illustrate another embodiment of a light source disinfecting system 180 that may be incorporated into a PTS 10. More specifically, the light source disinfecting system 180 may be incorporated into a pneumatic tube such that air passing through the pneumatic tube (e.g., under pressure or vacuum) is disinfected. As best shown in FIGS. 6A and 6B the light source disinfecting system 180 includes a pneumatic tube section 210 having a diameter that is the same as the diameter of the pneumatic transport tubes of the PTS. In this regard, the internal bore 212 of the tube section 210 shares a common diameter with the pneumatic tubes of the system 10 and permits the passage of a pneumatic carrier there through. In one embodiment, the tube section 210 is formed of similar materials that are utilized with the remainder of the pneumatic tube system (e.g., stainless steel). However, it will be appreciated that in other embodiments the tube section 210 may be formed of other materials (e.g., plastics, composites, etc.).

The tube section 210, in the present embodiment, includes a two light apertures or ports 214A and 214B. As shown, these ports 214A and 214B extend through the sidewall of the tube section 210. In the present embodiment, the ports 214A and 214B are generally rectangular. It will be appreciated that in other embodiments other port/aperture configurations may be utilized. For instance, a plurality of circular holes may be utilized. What is important is that the ports 214A and 214B of the tube section provide line of sight access for UV light sources 160. As shown, the UV light sources are disposed in a housing 220 that attaches to the tube section. As shown in the cross-sectional view of FIG. 6B, when the housing is attached to the tube section 210, the light sources are disposed proximate to the ports 214A and 214B such that UV light bathes the interior of the tube section 210. Accordingly, air passing through the tube is exposed to UV light.

The housing 220 attaches to the outside surface of the tube section 210 in a manner to reduce or eliminate pressure loss. That is, the housing acts as a pressure jacket to maintain airflow through the tube section 210. However, the housing need not be pressure tight; some air leakage is acceptable. In the present embodiment, the two ports 214A and 214B are spaced around a center axis of the tube section 210. However, it will be appreciated that the size, number and spacing of these ports may be selected to allow for a desired number and/or spacing of UV light sources 160.

While the size, number and spacing of the ports 214A, 214B (hereafter 214 unless specifically referenced) may be selected based on UV light requirements, it will be appreciated that such sizing and spacing may also be dependent upon the dimensions of the carriers utilized by the system. For instance, it may be desirable that the length of the ports 214 through the tube section 210 be shorter than the distance between the first and second wear bands 60, 62 of the carrier 50 utilized by the PTS. In this regard, at least one wear band of the carrier (which typically has two wear bands) will always be in contact with a solid portion of the tube section when passing there through. This lessens the likelihood of air passing around a carrier. Stated otherwise, limiting the axial length of the ports to less than the distance between the wear bands of a carrier lessens the likelihood of the carrier becoming stuck in the tube section 210. Generally, the limiting the width of the ports 214 in the tube section 210 permits a carrier to pass through unobstructed as there is enough structure between the ports 214 to maintain a proper orientation of a carrier passing there through.

As illustrated in FIG. 6C, the tube section 210 of the light source disinfecting system 180 is adapted to be disposed in-line with first and second pneumatic tube sections 70A and 70B. In this regard, a carrier 50 passing through the tube sections 70A and 70B may pass through the light source disinfecting system 180. However, it will be appreciated that carriers sometimes transport materials that may be adversely affected by UV light. That is, carriers routinely carry biological samples (e.g., blood etc.), which may be affected by UV light. Furthermore, many pneumatic carriers are at least partially translucent. Accordingly, biological samples carried within such partially translucent carriers may be exposed to the UV light sources 160 absent remedial measures. To alleviate such concerns, one embodiment of the present system utilizes the ID chip 52 of the carrier 50 to deactivate and reactivate the UV light sources 160 of the light source disinfecting system 180. In such embodiment, one or more antennas 40 or other proximity sensors identify the presence of an approaching carrier and deactivate the UV light sources 160 prior to the carrier 50 passing through the light source disinfecting system 180. See FIG. 6D. Once the carrier 50 has passed through the light source disinfecting system 180, the UV light sources 160 may be reactivated. See FIG. 6E. Such an embodiment allows for disinfecting air as it passes through the pneumatic tubes while preventing unwanted application of UV light two carriers as a pass-through the PTS.

As will be appreciated, the in-line light source disinfecting system 180 may be implemented various locations throughout a PTS. For instance, the in-line light source disinfecting system 180 may be disposed above a user station 18 within the PTS such that all air entering from or venting to the user station location is disinfected. See FIG. 6F. Likewise, the in-line light source disinfecting system may be located at various intermediate locations (i.e., locations between user stations) throughout the PTS.

Another concern in a PTS is the existence of pathogens on the interior surfaces of pneumatic system components such as pneumatic tubes. For instance, if a carrier leaks during transport, it may be desirable or necessary to clean the interior of the pneumatic tubes through which the carrier has passed. To date, the only known method of cleaning the interior of a PTS pneumatic tube involves the use of liquid cleaning agents/solutions. The administration of these liquid cleaning agents is generally unregulated or passively regulated and the dispersal of these agents is contingent on pneumatic tube lengths. Lines at or near the introduction area of the liquid cleaning solution can receive copious amounts of the solution while more distal pneumatic tube locations may receive little or no effective cleaning solutions. Furthermore, the effectiveness of this method is conditional on the correct mix of the cleaning solutions along with the standing time needed to kill the pathogens being targeted. Currently, there is no measure in the industry to gauge the effectiveness of the use of any liquid-based cleaning solution as applied in the pneumatic tube environment.

Figure 7:
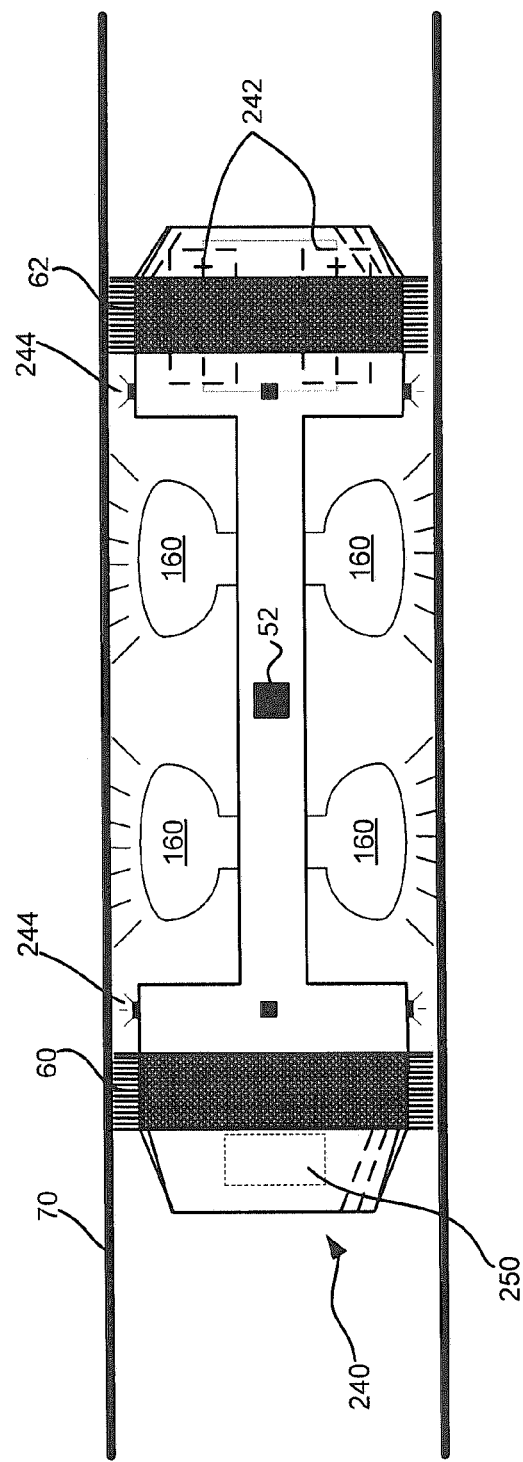
FIG. 7 illustrates another UV light source disinfecting system adapted for transport through a pneumatic tube system.

FIG. 7 illustrates another embodiment of a light source disinfection system that allows for disinfecting interior surfaces of a PTS. As shown, the light source disinfection system is a modified carrier or UV carrier 240, which is operative to transit through pneumatic tubes and PTS components (e.g. TCUs, transfer units, etc.). As with the carrier described in relation to FIG. 3, the UV carrier includes first and second wear bands 60, 62 that are sized to snuggly fit within the inside surface of a pneumatic tubes 70. These wear bands, in conjunction with the generally solid ends of the carrier body, substantially block the passage of air across the UV carrier 240 when disposed within a pneumatic tube. Accordingly, the UV carrier may transit through a PTs in a manner substantially identical to a standard carrier. However, instead of including a cargo enclosure, the UV carrier 240 supports one or more UV light sources 160. As shown, the UV light sources 160 are supported along a mid-section of the UV carrier 240 between the first and second wear bands 60, 62. However, the UV light sources 160 may be disposed at other locations (e.g., front or rear end caps of the UV carrier). Also supported within the UV carrier is a power supply 242 (e.g., batteries), which is electrically connected to the UV light sources (connections not shown for clarity).

During operation, the UV carrier is placed in a user station and launched into the PTS 10. Once within the confines of the PTS, the UV light sources 160 are activated to generate UV light, which is applied to interior surfaces of the PTS. As illustrated in FIG. 7, the light is applied to the interior surface of a pneumatic tube 70, however, such UV light may be applied to interior surfaces of other PTS components as well. To prevent operation of the UV light sources before the UV carrier 240 is within the confines of the PTS, one embodiment of the UV carrier utilizes one or more proximity sensors 244 (e.g., photo-detectors). These proximity sensors prevent activation of the UV light sources 160 if the UV carrier is not disposed within the confines of the PTS. As will be appreciated, in UVGI systems the UV lamps are typically shielded to limit exposure. That is, germicidal wavelengths of UV light can produce sunburn and exposure of eyes to this UV radiation can produce cornea inflammation. Accordingly, the UV carrier may be designed to be inoperable unless disposed within the confines of a PTS. The proximity sensors 244 may thus prevent initial activation of the UV light sources 160 unless one or all of the proximity sensors 244 is within a predetermined distance of a confining surface (e.g., inside surface of a pneumatic tube). Once all sensors are disposed within the predetermined distance of a confining surface, the UV light sources 160 may be activated. In embodiments utilizing the proximity sensors, the UV carrier may further include a control circuit 250 to operate the sensors and light sources.

The UV carrier may further include an ID chip 52, which allows tracking the UV carrier throughout a PTS. In this regard, one or more UV carriers may be routed (e.g., automatically) through every pneumatic tube and PTS component of a PTS. That is, the System Central Controller 8 (SCC; see FIG. 2) may be operative to route one or more UV carriers throughout the entire PTS to periodically disinfect the PTS. Alternatively, the SCC may have automatically route one or more UV carriers through each system tube and component on a scheduled basis. That is, disinfection may be performed without use of a carrier tracking system. Further, users may selectively route the UV carrier through the PTS.

The effectiveness of germicidal UV depends on a number of factors: the length of time a pathogen is exposed to UV, power fluctuations of the UV source and a pathogen's ability to withstand UV during its exposure. Accordingly, when utilizing a UV carrier 240 to disinfect interior components of a PTS, it may be desirable to move the UV carrier 240 at a predetermined speed to provide desired disinfection. That is, providing sufficient exposure to UV light may require a UV carrier move at or below a predetermined transit speed to allow sufficient exposure to provide disinfection. Further, such a predetermined transit speed may depend upon the intensity of UV light, length of exposure (which may be a function of the distance between wear bands of UV) and/or number of UV light sources and/or pathogens being targeted. Accordingly, it may be desirable for the UV carrier 240 to move at a transit rate that is slower than standard carriers in a PTS. That is, it may be desirable or necessary to alter the speed of the UV carrier. Accordingly, in one embodiment, the power of the blower (see FIG. 1) is variably controlled to maintain a predetermined air flow speed throughout a pneumatic path. Such variable control may entail altering the power applied to the blower to generate a desired airflow velocity in a pneumatic path and/or monitoring transit speed of a UV carrier (e.g., utilizing the ID chip 52 and one or more antennas/readers). Such a variable control system is set forth in co-owned U.S. Pat. No. 7,950,879, the entire contents of which is incorporated herein by reference.

Figure 8:
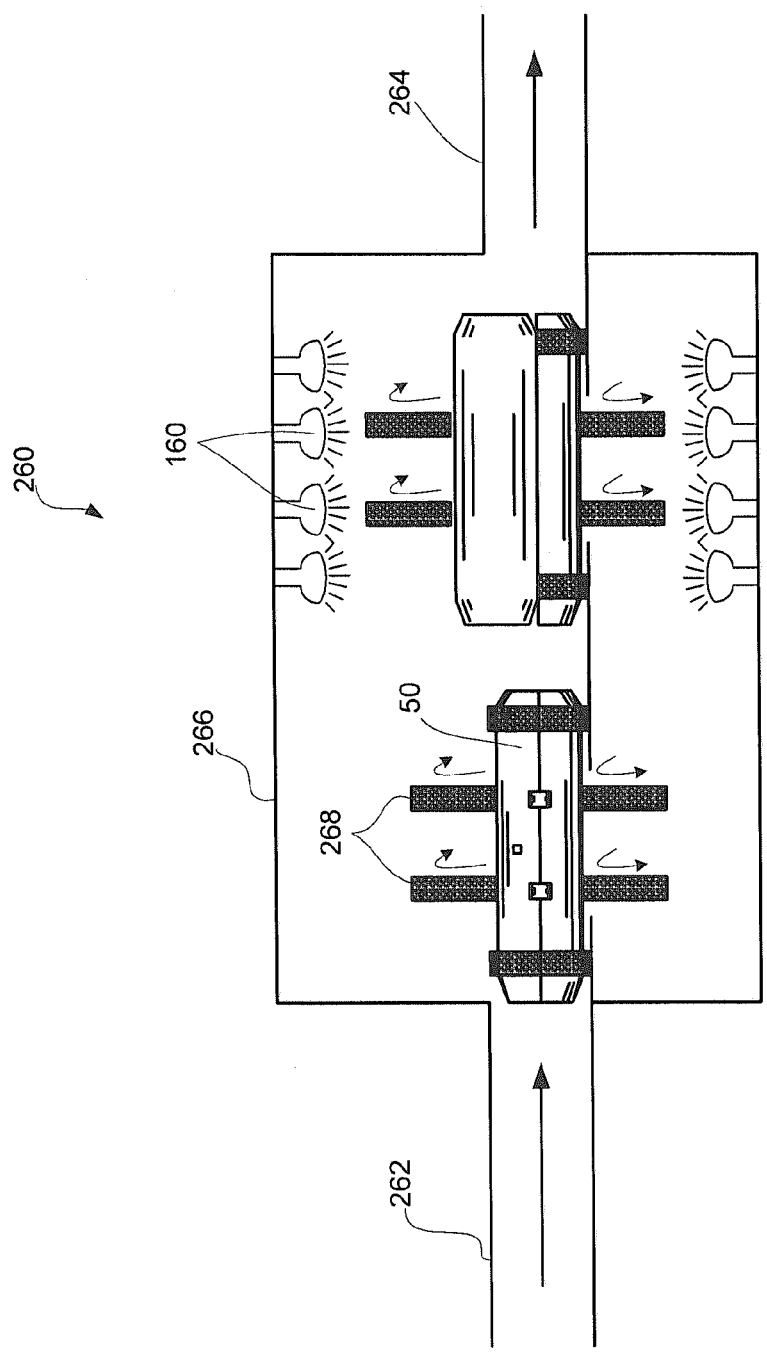
FIG. 8 illustrates another UV light source disinfecting system adapted for disinfecting pneumatic carriers.

FIG. 8 illustrates another embodiment of a light source disinfection system 260 that allows for disinfecting PTS carriers 50. That is, it has been recognized that the exterior and/or interior surfaces of carriers, like PTS components, may be subject to pathogen contamination. Accordingly, it may be desirable to periodically disinfect the exterior and/or interior of the carriers. If opaque carriers are utilized with the PTS, an in-line light source disinfecting system 180 as described in relation to FIGS. 6A-6F may be utilized. However, in many systems, translucent or transparent carriers are utilized to allow users to easily identify if a carrier includes a payload. In such systems, it may be desirable to only disinfect (e.g., exterior and/or interior) empty carriers. That is, it may be desirable to limit UV exposure of carrier to those carriers that do not contain contents.

As illustrated in FIG. 8, the light source disinfecting system 260 is a pneumatic tube system component that may be integrated into a PTS. In this regard, the light source disinfecting system 260 includes at least a first receiving tube 262 that is connectable to a PTS. The receiving tube 262 allows for receiving and or dispatching carriers from the PTS. In the illustrated embodiment, the light source disinfecting system 262 further includes a dispatch to 264. Once incorporated into a PTS, carriers 50 may be periodically directed to the light source disinfecting system 260. That is, the system controller may utilize transaction records indexed carrier identifications to schedule carrier disinfection. In one embodiment, carriers may be dispatch to the light source disinfecting system 260 after predetermined number of carrier transactions. In another embodiment, carriers may be dispatch to the light source disinfecting system 260 on a scheduled basis (e.g., every day, every two days, etc.). Likewise, carriers may be dispatch the light source disinfecting system 260 after each delivery to a predetermined location. For instance, each time a carrier is utilized deliver a payload to a laboratory in a hospital setting that carrier may subsequently be sent to the light source disinfecting system 260. Further, as the light source disinfecting system 260 is a system component of a PTS, users may direct carriers to the light source disinfecting system. That is, using inputs on the user station, a user may direct a carrier to light source disinfecting system 260.

As shown, the light source disinfecting system 260 includes an enclosed housing 266 which houses various UV light sources 160. In the present embodiment, the light source disinfecting system 260 includes a plurality of rollers 268 which engage the outside surface of the carrier 50 upon receipt. These rollers are operative turned the carrier 50, unlatch the carrier latches and subsequently open the carrier 50. In this regard, the interior of the carrier is exposed and UV light from the UV light sources 160 may be applied to both the interior and exterior of the carrier. After application of UV light to the carrier, the rollers at 68 may be utilized to close the carrier and dispatch the carrier back to the PTS. In the latter regard, the carrier may be dispatched to a empty carrier storage location or to an assigned location within the PTS.

The foregoing description of the presented inventions has been presented for purposes of illustration and description. Furthermore, the description is not intended to limit the inventions to the forms disclosed herein. Consequently, variations and modifications commensurate with the above teachings, and skill and knowledge of the relevant art, are within the scope of the presented inventions. For instance, it will be appreciated that various aspects of each the disclosed embodiments may be incorporated into the other embodiments. For instance, ion generators and/or filters discussed in relation to the first embodiment may be incorporated into the light source disinfecting system of FIG. 8. The embodiments described hereinabove are further intended to explain best modes known of practicing the inventions and to enable others skilled in the art to utilize the inventions in such or other embodiments and with various modifications required by the particular application(s) or use(s) of the presented inventions. It is intended that the appended claims be construed to include alternative embodiments to the extent permitted by the prior art.

What is claimed is:

1. A system for at least partially disinfecting airflow in a pneumatic tube system, comprising:
   a pneumatic tube system including at least a first user station having a first pneumatic tube, a second user station having a second pneumatic tube and at least one transfer device for selectively aligning one of said first and second pneumatic tubes with an airflow;
   a blower connectable to said pneumatic tube system, wherein said blower is operative to provide air flow through at least a portion of said pneumatic tube system, said blower including:
      a first port fluidly connected to said pneumatic tube system for supplying said air flow to said pneumatic system components;
      a second port for venting air from said blower and drawing air into said blower; and
   a light source disinfecting system interconnected to said second port, said light source disinfection system including at least one UV light source, wherein air venting from said blower or drawing into said blower is exposed to UV light from said UV light source.

2. The system of claim 1, wherein said light source disinfecting system further comprises:
   a housing having:
      an at least partially enclosed interior, wherein said at least one light source is disposed in said interior of said housing;
      an first inlet/outlet opening exposed to atmosphere; and
      a second inlet/outlet opening connected to said second port of said blower.

3. The system of claim 2, wherein a length of said housing between said first inlet/outlet opening and said second inlet/outlet opening is sized to permit airflow venting from said blower or drawing into said blower be exposed to said UV light for at least 0.1 milliseconds.

4. The system of claim 1, wherein said at least one UV light source comprises:
   a pulsed Xenon light source.

5. The system of claim 4, wherein light pulses of said Xenon UV light source are between about 0.1 milliseconds and about 3 milliseconds in duration.

6. The system of claim 1, wherein said light source disinfection system further comprises:
   an ion generator.

7. A system for at least partially disinfecting airflow in a pneumatic tube system, comprising:
   a tube section having an internal bore at least partially defined by a sidewall extending between a tube inlet and a tube outlet, wherein the internal bore has an internal diameter that is sized to accommodate the passage of a pneumatic carrier there through and wherein the sidewall includes at least a first aperture;
   at least a first UV light source supported proximate to said first aperture, wherein UV light from said UV light source is directed into said internal bore of said tube section;
   a housing adapted to support said first UV light source proximate to said first aperture, wherein said housing engages at least a portion of an exterior surface of the tube section, wherein said first aperture is disposed within said housing; and
   a pneumatic tube station adapted to send and receive pneumatic carriers to and from the pneumatic tube system, said pneumatic tube station having a sending/receiving tube interconnected to said tube section, wherein at least a portion of air accompanying the pneumatic carriers sent and received by the pneumatic tube system is exposed to said UV light source.

8. The system of claim 7, wherein said tube inlet is connected to a first pneumatic tube and said tube outlet is connected to a second pneumatic tube, wherein internal bores of said first and second pneumatic tubes are aligned with said internal bore of said tube section.

9. The system of claim 8, further comprising:
   a controller operative to activate and deactivate said UV light source; and
   a least one proximity sensor operative to identify a presence of a pneumatic carrier in one of said first pneumatic tube, said second pneumatic tube and said tube section, wherein said controller is further operative to deactivate said UV light source based on a detected presence of said a pneumatic carrier.

10. The system of claim 7, wherein said UV light source comprises;
   a pulsed Xenon UV light source.

11. The system of claim 10, wherein pulses of said Xenon UV light source are between about 01. milliseconds and about 3 milliseconds in duration.

12. The system of claim 7, wherein at least a portion of air drawn into said pneumatic tube system from said pneumatic tube station is exposed to said first UV light source.

13. The system of claim 12, wherein at least a portion of air expelled from said pneumatic tube system out of said pneumatic tube station is exposed to said first UV light source prior to being expelled.

14. A system for at least partially disinfecting airflow in a pneumatic tube system, comprising:
   a tube section having an internal bore at least partially defined by a sidewall extending between a tube inlet and a tube outlet, wherein the internal bore has an internal diameter that is sized to accommodate the passage of a pneumatic carrier there through and wherein the sidewall includes at least a first aperture and wherein said tube inlet is connected to a first pneumatic tube and said tube outlet is connected to a second pneumatic tube, wherein internal bores of said first and second pneumatic tubes are aligned with said internal bore of said tube section;

at least a first UV light source supported proximate to said first aperture, wherein UV light from said UV light source is directed into said internal bore of said tube section;

a housing adapted to support said first UV light source proximate to said first aperture, wherein said housing engages at least a portion of an exterior surface of the tube section, wherein said first aperture is disposed within said housing;

a controller operative to activate and deactivate said UV light source; and a least one proximity sensor operative to detect a presence of a pneumatic carrier in one of said first pneumatic tube, said second pneumatic tube and said tube section, wherein said controller is further operative to activate and deactivate said UV light source based on a detected presence of said a pneumatic carrier.

* * * * *